US012653735B1

(12) United States Patent
Snyder

(10) Patent No.: US 12,653,735 B1
(45) Date of Patent: Jun. 16, 2026

(54) WHEELCHAIR MANEUVER ASSIST DEVICE

(71) Applicant: Eric Snyder, Jackson, NJ (US)

(72) Inventor: Eric Snyder, Jackson, NJ (US)

( * ) Notice: Subject to any disclaimer, the term of this patent is extended or adjusted under 35 U.S.C. 154(b) by 910 days.

(21) Appl. No.: 17/814,663

(22) Filed: Jul. 25, 2022

(51) Int. Cl.
 *A61G 5/10* (2006.01)
 *A61F 5/37* (2006.01)
(52) U.S. Cl.
 CPC .............. *A61G 5/10* (2013.01); *A61F 5/3776* (2013.01)
(58) Field of Classification Search
 CPC ................................ A61F 5/3776; A64G 5/10
 USPC ............... 280/304.1, 480, 801.1, 801.2, 808
 See application file for complete search history.

(56) References Cited

U.S. PATENT DOCUMENTS

| | | | |
|---|---|---|---|
| 2,556,121 A | 6/1951 | Thomas | |
| 7,021,644 B1 * | 4/2006 | Master ..................... | B60D 1/18 280/480 |
| 9,351,901 B1 | 5/2016 | Petsch | |
| 2013/0106077 A1 | 5/2013 | Nagel | |
| 2023/0106104 A1 * | 4/2023 | Landis ................... | B60D 1/187 280/480 |
| 2024/0016682 A1 * | 1/2024 | Swearingen ......... | A61G 7/1023 |

FOREIGN PATENT DOCUMENTS

| | | |
|---|---|---|
| CA | 2278889 | 5/2000 |
| CA | 3126948 | 7/2020 |

* cited by examiner

*Primary Examiner* — Valentin Neacsu
*Assistant Examiner* — Felicia L. Brittman-Alabi
(74) *Attorney, Agent, or Firm* — Reinier Smit

(57) ABSTRACT

A wheelchair maneuver assist device capable of attaching to a pair of handle grips to assist a caregiver or patient in maneuvering a wheelchair. The device includes a housing assembly and a strap assembly positioned within the housing assembly. The housing assembly further includes a lateral housing and a medial housing for partially protecting the strap assembly and providing rigidity to the device. The strap assembly further includes a lateral strap with at least one connector located at two distal ends and a medial strap having a handle located at the distal end. The connector is configured to span and attach to the pair of handle grips and the handle is configured to be grasped or connected to the caregiver or patient to enable the wheelchair to be pulled forward while the patient and/or caregiver is positioned in front of the wheelchair.

19 Claims, 8 Drawing Sheets

45

WHEELCHAIR MANEUVER ASSIST DEVICE

FIELD OF THE INVENTION

The disclosure herein pertains to wheelchair accessories, and more particularly, to a wheelchair maneuver assist device configured to connect to a pair of handle grips of a wheelchair for assisting a caregiver maneuver a wheelchair behind a patient while the caregiver maintains a position alongside the patient.

DESCRIPTION OF THE PRIOR ART AND OBJECTIVES OF THE INVENTION

Wheelchairs are one of the most essential devices used during mobility rehabilitation. Mobility rehabilitation is a form a physical therapy aimed at treating patients with mobility issues that may be the result of genetics, injury, wear-and-tear, old age, or surgery. While undergoing mobility rehabilitation, patients must relearn to stand up and walk by performing simple physical exercises that reinforce the strength and muscle memory necessary for proper mobility. If a patient's strength, mobility, and or coordination is poor, a caregiver will typically follow a walking patient with a wheelchair as the patient performs simple physical exercises, such as walking in a straight line. If the patient must sit down, because of fatigue or some other medical emergency, the caregiver pushing the wheelchair may position the wheelchair below the patient's buttocks, allowing the patient to safely descend into and sit in the seat of the wheelchair.

During mobility rehabilitation gait belts are also commonly used to assist a patient during rehabilitation by providing additional support to the patient as the patient performs physical movements such as standing up or walking. The gait belt is fastened around the patient and typically contains portion that allows a caregiver to grab onto the gait belt to assist and control the patient's physical movement and follow alongside the patient to improve the patient's safety. If the patient's condition requires, the gait belt may be used in combination with a wheelchair to provide the maximum amount of protection in situations where the patient needs to abruptly sit down. Although the practice of using a gait belt in combination with a wheelchair provides the ideal protection against an unexpected fall, it also requires two caregivers—one caregiver walking alongside the patient and grabbing onto the gait belt, and a second caregiver pushing the wheelchair behind the patient as they perform physical exercises.

By 2030, all Baby Boomers will be at least sixty-five and therefore as the number of patients seeking mobility rehabilitation increases, the number of caregivers required to properly care for patients must also increase. During times of low employment or high employee cost, rehabilitation services are likely facing the challenge of being understaffed resulting in staffing shortages that make it difficult to provide the ideal number of caregivers to ensure patient safety. If only one caregiver is available, it becomes increasingly difficult to walk alongside properly and safely to assist a patient as the patient performs physical movements such as standing up or walking. In this situation, the caregiver must decide between using the gait belt without the wheelchair following behind, or they push the wheelchair behind the patient without a gait belt. In some situations, the caregiver may even decide to use both devices improperly which may exacerbate the potential risk that the patient will fall. In these situations, the caregiver typically contorts themselves in awkward positions in order to pull the wheelchair forward while maintaining contact with the patient, which increases the likelihood of causing pain or discomfort to themselves in the process of attempting to assist the patient.

Wheelchairs provide seating and postural support for patients, especially patients who suffer from lower back and leg injuries. Proper postural support is a crucial factor in the recovery of patients. The surfaces of the seat and backrest of the wheelchair are designed to minimize sensitive pressure areas that tend to cause extreme discomfort and pain for patients who spend a lot of time sitting in a wheelchair. The most common pressure sensitive areas include the top edge of the backrest and top surface of the seat. When a person sits in a wheelchair for a long time, they are more susceptible to developing pressure sores on their buttock, back of their thighs, and their back. Because every patient is unique, many wheelchairs are custom built and sized to facilitate the most comfortable wheelchair experience for the patient. A higher backrest would be more stable for the certain patients; however, it becomes more challenging for those patients to propel themselves forward because the high backrest may interfere with the movement of and place unnecessary pressure on their shoulder blades. A wider seat would also be more stable and comfortable for the patient; however, this too becomes more challenging for the patient and caregiver to propel and navigate the wheelchair forward. Regardless of the dimensions of the backrest and seat portion of the wheelchair, one of the most effective ways to avoid the creation of pressure sensitive areas is to maintain a smooth and comfortable seat and backrest surface. Any additional accessories that may be attached to the wheelchair must avoid these surfaces and should not increase or create any pressure sensitive areas on the seat or backrest surface.

Thus, in view of the problems and disadvantages associated with prior art devices, the present disclosure was conceived and one of its objectives is to provide a wheelchair maneuver assist device enabling a single caregiver to walk alongside a patient to safely assist the patient during physical movement, guard the patient from falling, and pull a wheelchair directly behind the patient in case the patient needs to sit down because of fatigue or some other medical emergency.

It is another objective of the present disclosure to provide a wheelchair maneuver assist device that, when attached to the wheelchair and stowed, does not obstruct the seat or backrest surface of the wheelchair.

It is still another objective of the present disclosure to provide a wheelchair maneuver assist device that provides a lateral pushing surface that is more in line with a caregiver's natural push stroke.

It is yet another objective of the present disclosure to provide a wheelchair maneuver assist device that attaches to a wheelchair and can be quickly stowed away without obstructing a patient's ability to comfortably sit in the wheelchair.

It is a further objective of the present disclosure to provide a wheelchair maneuver assist device that is easy to use, and simple to manufacture and repair using widely available components.

It is still a further objective of the present disclosure to provide a wheelchair maneuver assist device that remains attached to the wheelchair when the wheelchair maneuver assist device is not in use and can be inconspicuously stowed away within the footprint of the wheelchair.

It is yet a further objective of the present disclosure to provide a wheelchair maneuver assist device that attaches behind a backrest of a wheelchair and includes a strap that pivots over the seat when a caregiver is pulling the wheelchair and pivots back behind the seat when the wheelchair maneuver assist device is not in use.

It is another objective of the present disclosure to provide a wheelchair maneuver assist device that can be rotatably positioned over the seat of a wheelchair to provide a means for pulling the wheelchair behind a patient while the patient is performing a physical rehabilitation exercise and can be rotatably positioned to dangle behind the seat of a wheelchair so as to not obstruct the seat or backrest while the patient is sitting down or the normal movement of the wheelchair.

It is yet another objective of the present disclosure to provide an ergonomic position for a caregiver to assist a patient with both hands in order to reduce the risk of pain, injury or any other musculoskeletal disorder to the caregiver or patient, while maneuvering a wheelchair to follow closely behind the patient during mobility rehabilitation.

It is an additional objective of the present disclosure to reduce the need for multiple caregivers to attend to a single patient in order to improve productivity of therapy staff and reduce the need of additional caregivers present during mobility rehabilitation.

Various other objectives and advantages of the present disclosure will become apparent to those skilled in the art as a more detailed description is set forth below.

SUMMARY OF THE INVENTION

The aforesaid and other objectives are realized by providing a wheelchair maneuver assist device enabling a single caregiver to pull a wheelchair behind a patient walking during mobility rehabilitation, while maintaining the proper position and contact alongside the walking patient. The wheelchair maneuver assist device enables a single caregiver to use both a gait belt and a wheelchair to provide the maximum amount of safety while providing rehabilitative care. The wheelchair maneuver assist device includes a strap assembly that further includes at least one lateral strap and at least one medial strap. The lateral strap includes at least two connectors located at distal ends of the lateral strap and configured to connect the lateral strap to a pair of wheelchair handle grips. The connector may include a single loop, plurality of loops (e.g., daisy chain), clips, hooks, screws, clamps, and so forth. The medial strap includes a handle located at a distal end of the medial strap and is rotatably connected to the lateral strap between the distal ends. The handle may include a single loop, plurality of loops (e.g., daisy chain), clip, buckle, or handle component configured to be gripped by or connected to the caregiver or patient. The handle is preferably grasped by a single hand of the caregiver; however, it shall be noted that the handle may also be configured to facilitate a connection between the medial strap and a gait belt worn by the patient. The lateral strap and medial strap join to form a generally T-shaped strap configuration. The lateral strap may be joined with the medial strap by stitching together the straps, tying together the straps, connecting the straps together with a strap connector, or any other method capable of forming the T-shaped strap configuration. The strap assembly is positioned within a housing assembly that includes a lateral housing and a medial housing. The lateral housing and medial housing join to form a rigid T-shaped conduit for the receipt of the strap assembly. The housing assembly protects the strap assembly against wear and tear and the lateral housing facilitates a surface that is more in line with the natural push stroke of the caregiver. The medial strap of the wheelchair maneuver assist device may be pulled, or the lateral housing of the wheelchair maneuver assist device may be pushed to propel the wheelchair forward.

When attached to the pair of handle grips, the wheelchair maneuver assist device may be configured into an in use, active phase, or a stowed, inactive phase. In instances where the caregiver must pull the wheelchair, the medial portion (i.e., the medial strap and medial housing) of the wheelchair maneuver assist device may be configured to rotate around the lateral portion (i.e., the lateral strap and lateral housing) of the wheelchair maneuver assist device such that the medial portion is positioned over a centerline of a seat of the wheelchair and the medial strap (i.e., the medial strap and medial housing) is pulled by the caretaker, the wheelchair follows behind the walking patient. In instances where the caregiver must push the wheelchair or the patient needs to sit in the seat of the wheelchair, the medial portion (i.e., the medial strap and medial housing) may be reconfigured to rotate back around the lateral portion (i.e., the lateral strap and lateral housing) such that the medial portion (i.e., the medial strap and medial housing) is positioned dangling towards the floor and behind a backrest of the wheelchair so that the wheelchair maneuver assist device does not obstruct the backrest or seat, which would make for an uncomfortable seating experience.

BRIEF DESCRIPTION OF THE DRAWINGS

FIG. 6 shows a side view of a wheelchair having the wheelchair maneuver assist device of FIG. 2 attached to a

5

Figure 1:
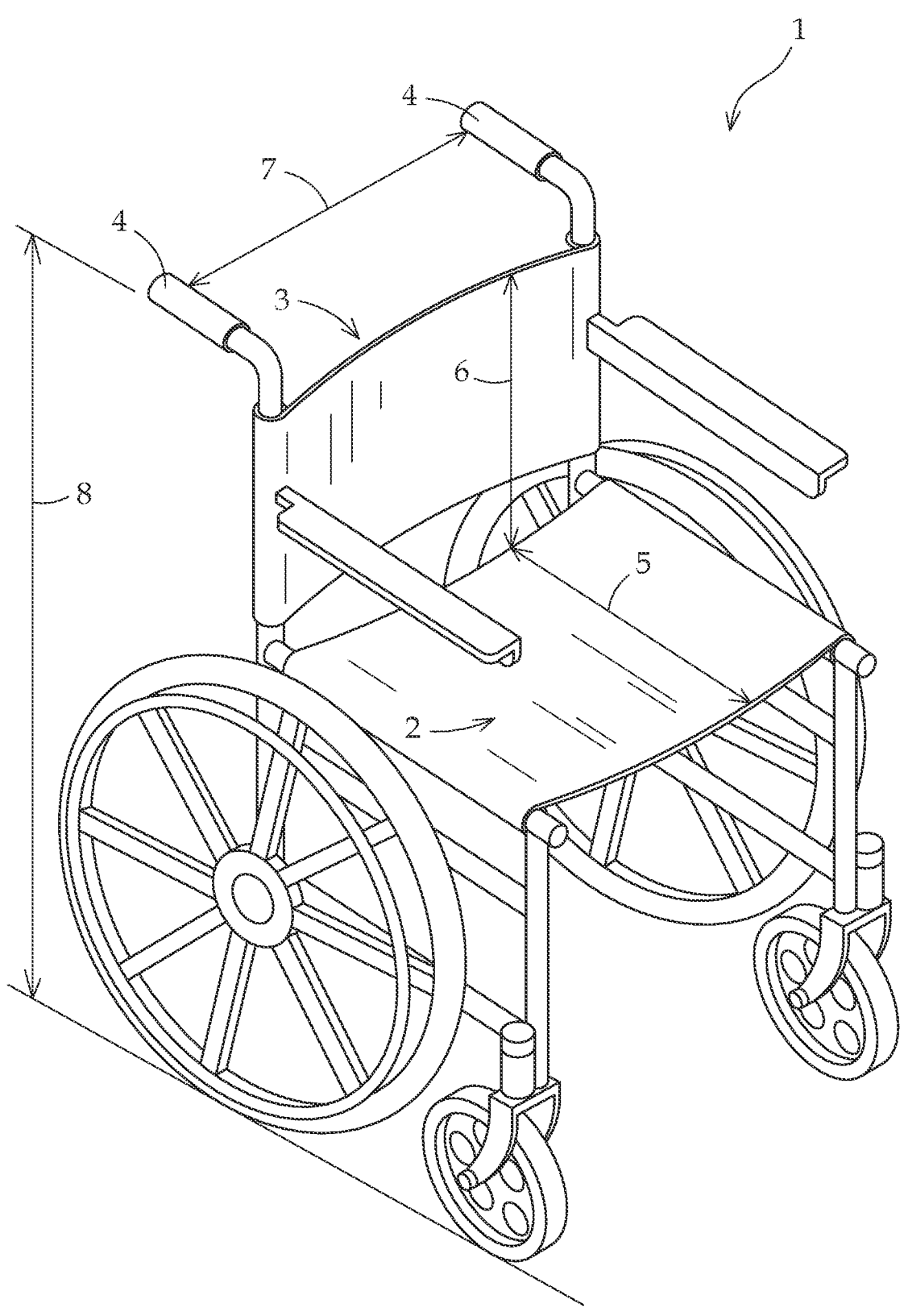
FIG. 1 demonstrates a side elevation view of a typical prior art wheelchair illustrating the seat, backrest, and the pair of handle grips.

6 pair of handle grips of the wheelchair and positioned in an inactive state, wherein the medial portion dangles plumb towards the floor and positioned behind a backrest of the wheelchair.

DETAILED DESCRIPTION OF THE PREFERRED EMBODIMENT AND OPERATION OF THE INVENTION

Various exemplary embodiments of the present disclosure are described below. Use of the term "exemplary" means illustrative or by way of example only, and any reference herein to "the disclosure" is not intended to restrict or limit the disclosure to exact features or step of any one or more of the exemplary embodiments disclosed in the present specification. References to "exemplary embodiment", "one embodiment", "an embodiment", "various embodiments", and the like may indicate that the embodiment(s) of the disclosure so described may include a particular feature, structure, or characteristic, but not every embodiment nec- essarily incudes the particular feature, structure, or charac- teristic. Further, repeated use of the phrase "in one embodi- ment", "in an exemplary embodiment", or "in an alternative embodiment" do not necessarily refer to the same embodi- ment, although they may.

It is also noted that terms like "preferably", "commonly", and "typically" are not utilized herein to limit the scope of the disclosure or to imply that certain features are critical, essential, or even important to the structure or function of the disclosure. Rather, these terms are merely intended to highlight alternative or additional features that may or may not be utilized in a particular embodiment of the present disclosure.

The present disclosure is described more fully hereinafter with reference to the accompanying figures, in which one or more exemplary embodiments of the disclosure are shown. Like numbers used herein refer to like elements throughout. The disclosure may, however, be embodied in many differ- ent forms and should not be construed as limited to the embodiments set forth herein; rather, these embodiments are provided so that this disclosure will be operative, enabling, and complete. Accordingly, the particular arrangements dis- closed are meant to be illustrative only and not limited as to the scope of the disclosure, and any and all equivalents thereof. Moreover, many embodiments such as adaptations, variations, modifications, and equivalent arrangements will be implicitly disclosed by the embodiments described herein and fall within the scope of the instant disclosure.

Although specific terms are employed herein, they are used in a generic and descriptive sense only and not for the purposes of limitation. Unless otherwise expressly defined herein, such terms are intended to be given their broad, ordinary, and customary meaning not inconsistent with that applicable in the relevant industry and without restriction to any specific embodiment hereinafter described. As used herein, the article "a" is intended to include one or more items. Where only one item is intended, the terms "one and only one", "single", or similar language is used. When used herein to join a list of items, the term "of" denotes at least one of the items but does not exclude a plurality of items of the list.

For exemplary methods or processes of the disclosure, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present disclosure.

Additionally, any references to advantages, benefits, unexpected results, or operability of the present disclosure are not intended as an affirmation that the disclosure has previously been reduced to practice or that any testing has been performed. Likewise, unless stated otherwise, use of verbs in the past tense (present perfect or preterit) is not intended to indicate or imply that the disclosure has previ- ously been reduced to practice or that any testing has been performed.

As used herein, the distal end shall be interpreted as the point of a member situated away from its central point or point of attachment to another member and the proximal end shall be interpreted as the point of a member situated near its central point or point of attachment to another member. As described herein, a T-shaped configuration contains a lateral component having two distal ends and a medial component having a distal end and a proximal end, wherein the proxi- mal end is connected to a central point of the lateral member and the distal end is situated away or opposite the proximal end.

Figure 4C:
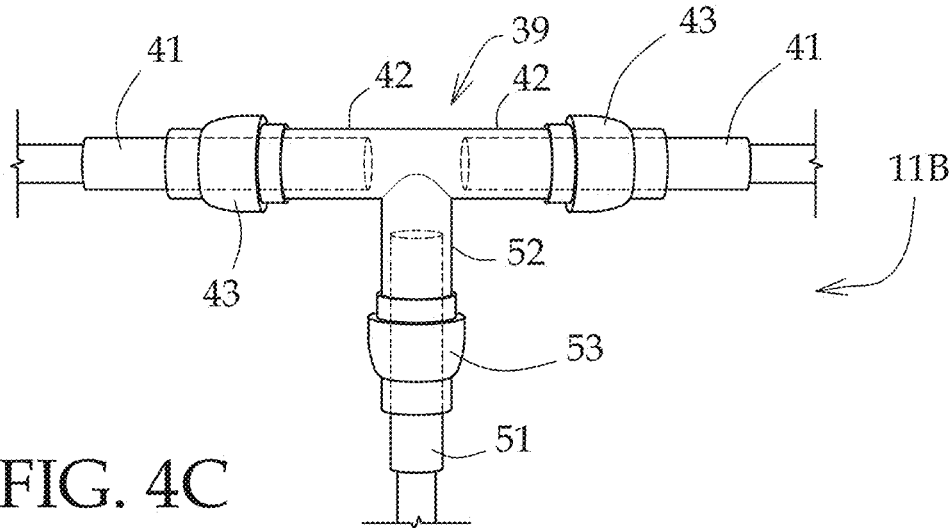
FIG. 4C demonstrates a top plan view of an alternative configuration of the preferred embodiment of FIG. 4B, wherein the housing assembly includes outer housing pipes and inner housing pipes configured to telescopically slide within the outer housing pipe.
Figure 4B:
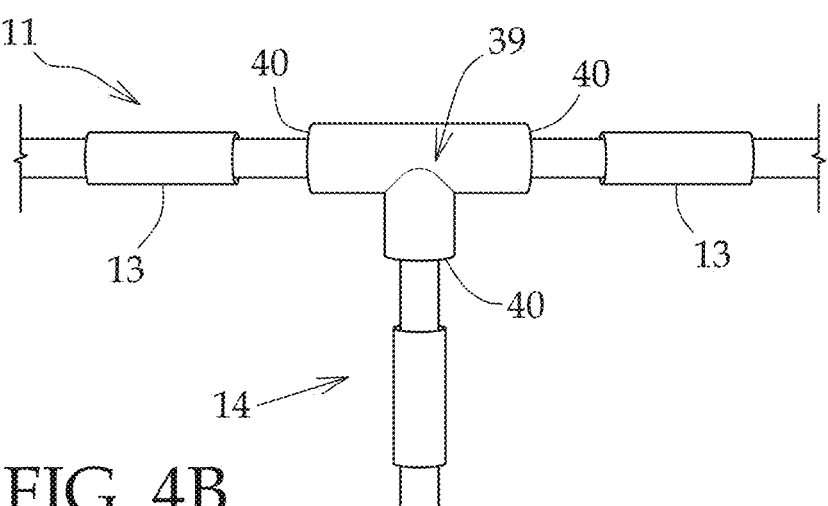
FIG. 4B demonstrates a top plan view of the preferred housing assembly, wherein a three-way, T-shaped housing link facilitates the connection between two lateral housing pipes and one medial housing pipe.
Figure 4A:
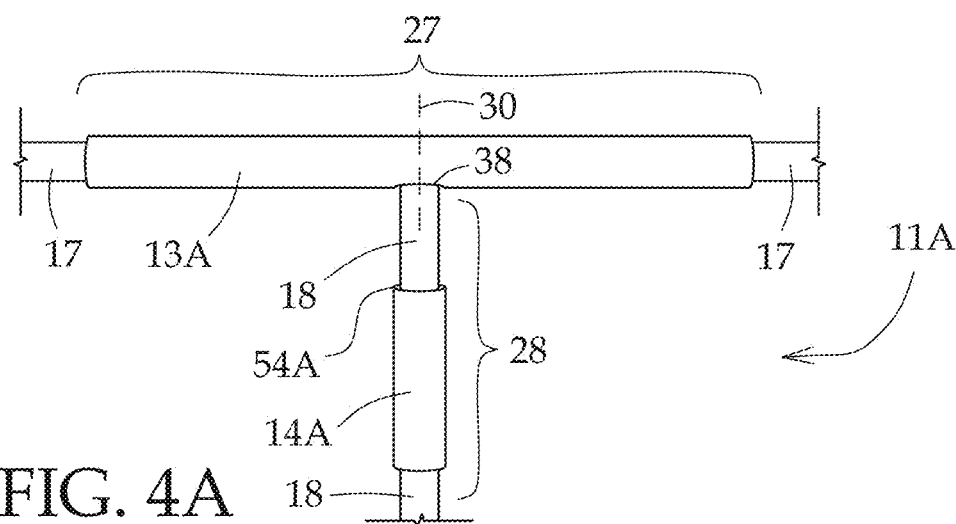
FIG. 4A demonstrates a top plan view of one housing assembly, wherein a proximal end of the medial housing is configured insertable within an opening defined near a center of the lateral housing.
Figure 5:
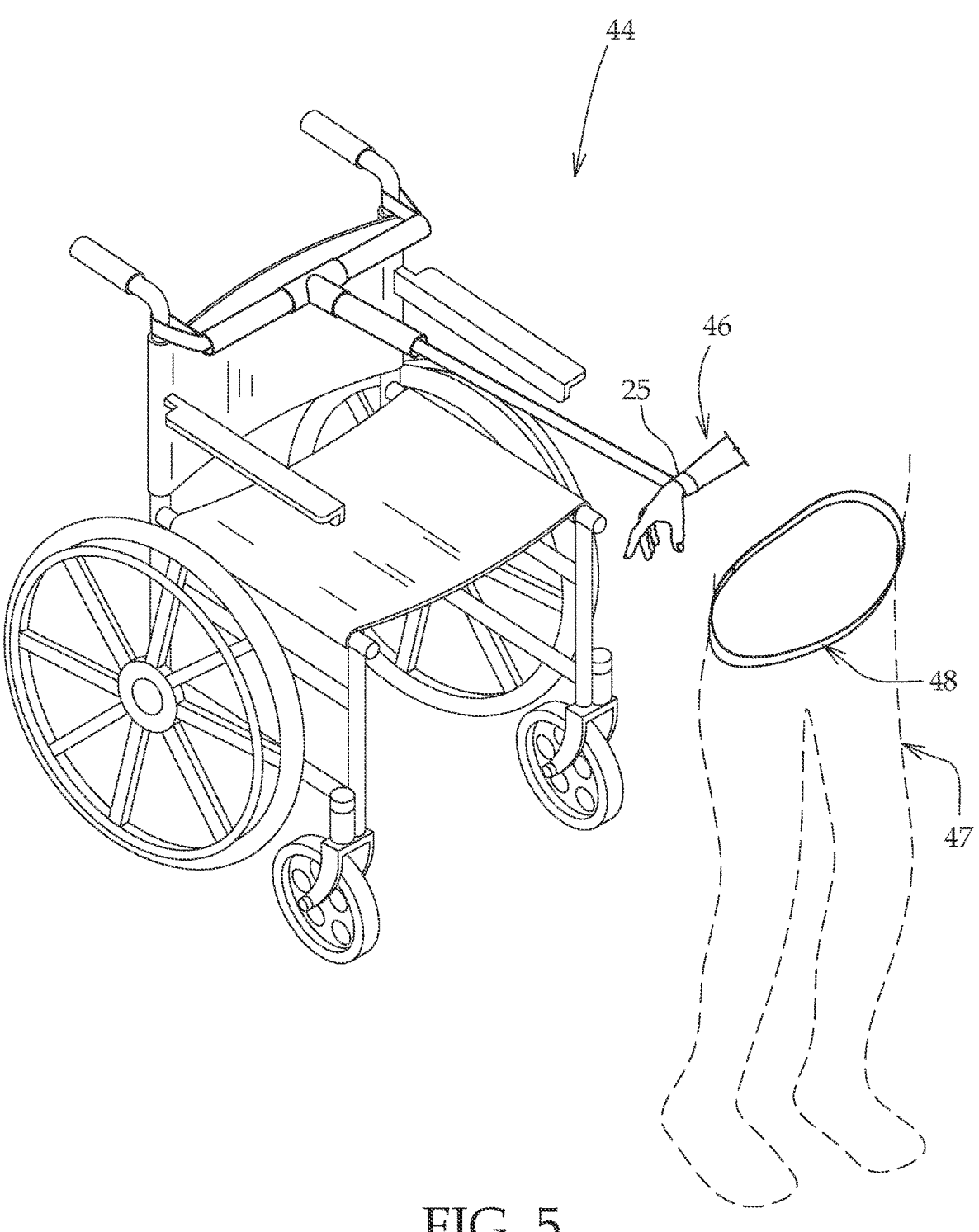
FIG. 5 features a side view of a wheelchair having the wheelchair maneuver assist device of FIG. 2 attached to a pair of handle grips of the wheelchair and positioned in an active state, wherein a caregiver pulls the medial strap of the wheelchair maneuver assist device while walking alongside a patient.
Figure 6:
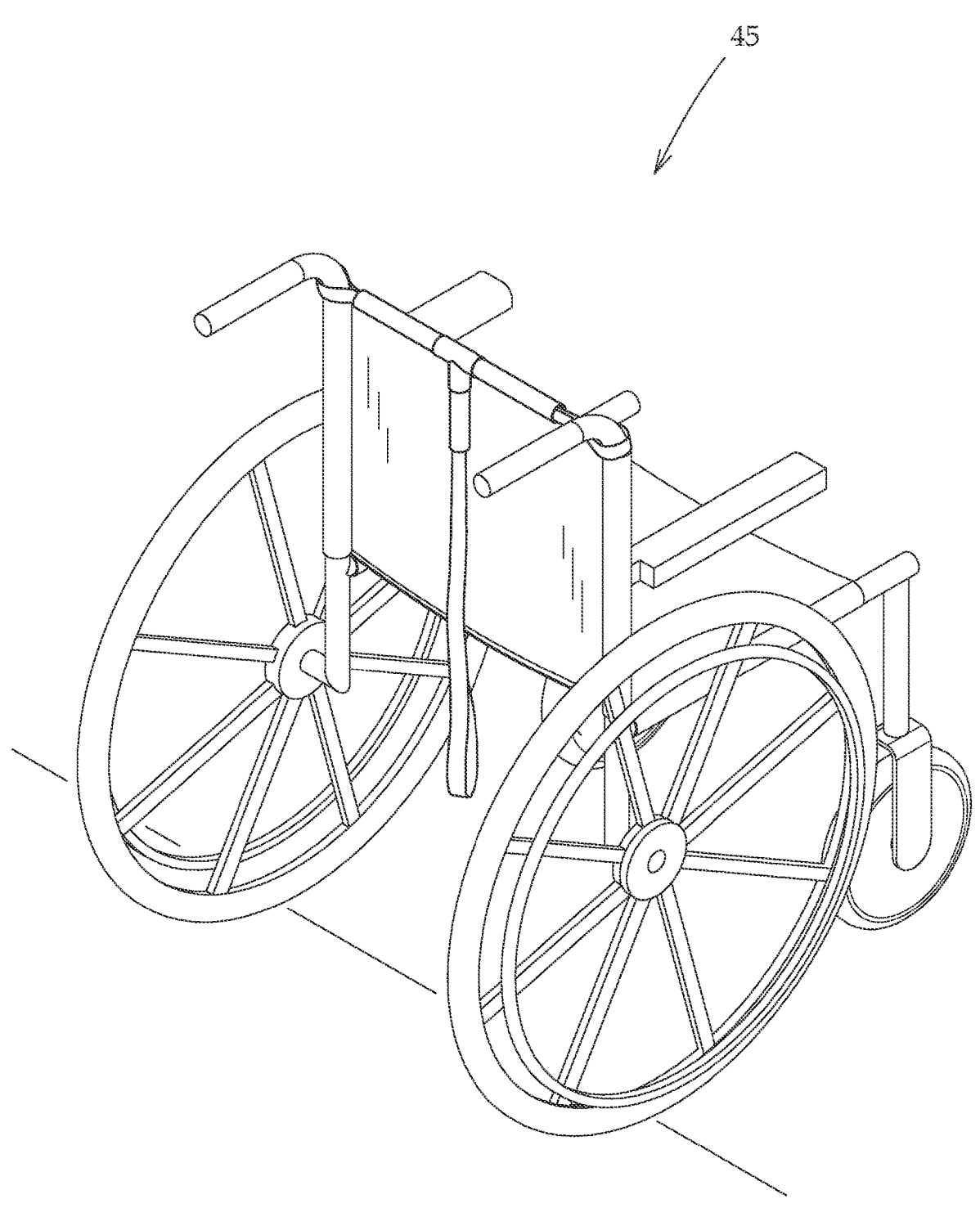

For a better understanding of the disclosure and its operation, turning now to the drawings, FIGS. 1-6 illustrate various views and orientations of the preferred embodiment of a wheelchair maneuver assist device 10. Throughout the description and figure illustrations, the wheelchair maneuver assist device 10, as seen in FIGS. 1-6, is represented as wheelchair maneuver assist device 10 for enabling a single caregiver 46 to correctly position themselves alongside a walking patient 47 as demonstrated in FIG. 5 and pull a wheelchair 1 directly behind the patient 47 to ensure the patient 47 may sit down in situations where the patient 47 becomes fatigued, requires a rest break, or suffers a medical emergency during mobility rehabilitation exercises. The wheelchair maneuver assist device 10 is attached to a pair of wheelchair handle grips 4 without increasing the overall footprint size (i.e., length, width, height) of the wheelchair 1 as seen in FIG. 1 or creating an uncomfortable seating experience for the patient 47. When the wheelchair maneu- ver assist device 10 is not needed to pull the wheelchair 1 forward, it may be reconfigured, without detaching from the handle grips 4 as seen in FIG. 6, into a stowed, or inactive state 45 where a medial portion 28 (i.e., a medial strap 18 and a medial housing 14) as seen in FIG. 4A is rotated around a lateral portion 27 (i.e., a lateral strap 17 and a lateral housing 13) such that the medial portion 28 is positioned dangling towards the floor and behind a backrest 3 of the wheelchair 1 so that the medial portion 28, espe- cially the medial strap 18, does not obstruct the backrest 3 or seat 2. Any obstruction or uneven surface on the seat 2 or backrest 3 makes for an uncomfortable seating experience increases the amount of pressure points on the patient 47, increases the risk of skin breakdown, and may affect the normal movement of the wheelchair 1.

As illustrated in the front perspective view of FIG. 1, a typical wheelchair 1 includes a seat 2, a backrest 3, and a pair of handle grips 4. The seat 2 is configured (i.e., sized, shaped, or otherwise capable of) to receive and support the buttocks of a patient 47 sitting in the wheelchair 1, and the seat 2 defines a seat depth 5. The seat depth 5 may vary based on the needs of the patient 47 that requires the wheelchair 1, such as height, weight, and the amount of postural support required. The backrest 3 is configured to receive and support the back of the patient 47 while sitting in the wheelchair 1, and the backrest 3 defines a backrest height 6. The backrest height 6 may vary based on the needs of the patient 47, such as height, weight, and the amount of postural support required. The pair of handle grips 4 are located behind the backrest 3 and are offset a distance from one another, defining a handle grip span 7. The handle grips 4 also are offset a distance from the floor, defining a handle grip height 8. Because many local, state, and federal laws and regulations attempt to follow a standardized wheelchair design, for example ISO 7176-7, many wheelchairs fit into design template above.

Figure 2:
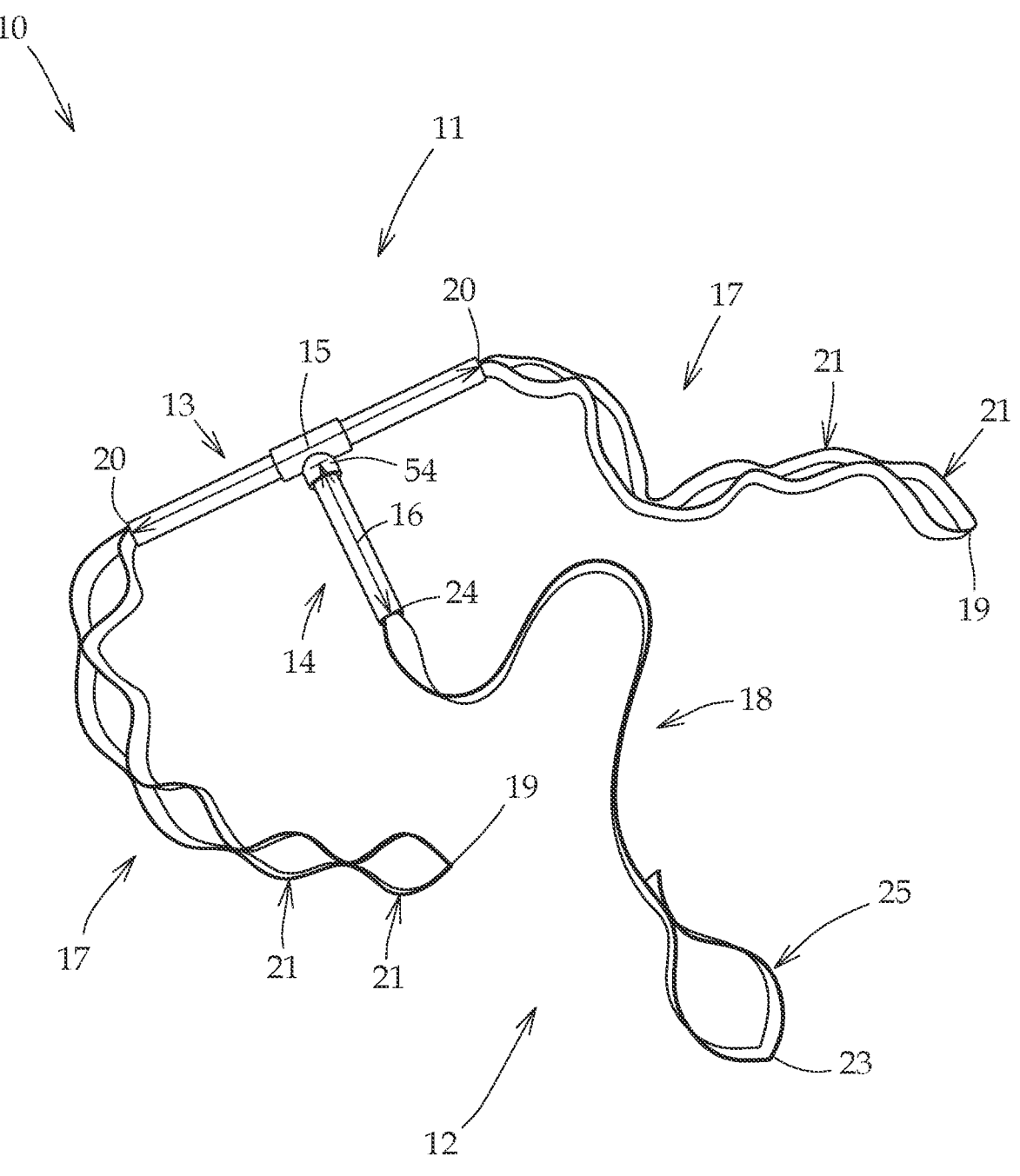
FIG. 2 shows a top plan view of the preferred embodiment of the wheelchair maneuver assist device.

As demonstrated in the top plan view of FIG. 2, wheelchair maneuver assist device 10 includes a housing assembly 11 and a strap assembly 12. The housing assembly 11 includes a lateral housing 13 configured to join a medial housing 14 to form a T-shaped conduit adapted to receive the strap assembly 12 to provide rigidity and to partially protect the strap assembly 12 from wear and tear. The lateral housing 13 preferably defines a lateral housing length 15 less than the handle grip span 7. The medial housing 14 preferably defines a medial housing length 16 less than the back rest height 6. The housing assembly 11 is made of a rigid material such as plastic, rubber, metal, wood, polymer, or a combination of these or other similar materials.

The strap assembly 12 includes a lateral strap 17 configured to join a medial strap 18 to form a T-shaped strap configuration. The lateral strap 17 is positioned through the lateral housing 13 with two distal ends 19 of the lateral strap 17 extending out of two distal ends 20 of the lateral housing 13. The lateral strap 17 further includes at least one connector 21 located at each of the distal ends 19 of the lateral strap 17 and configured to connect the lateral strap 17 between the pair of handle grips 4. The lateral strap 17 defines a lateral strap length 22 wherein the lateral strap length 22 is greater than the lateral housing length 15. The medial strap 18 is positioned through the medial housing 14 with a distal end 23 of the medial strap 18 extending out of a distal end 24 of the medial housing 14. The medial strap 18 further includes a handle 25 located at the distal end 23 of the medial strap 18 and configured to enable the caregiver 46 to grasp the handle 25, pull the medial strap 18, and propel the wheelchair 1 forward. The medial strap 18 defines a medial strap length 26 which is greater than the medial housing length 16. The wheelchair maneuver assist device 10 defines a lateral portion 27 and a medial portion 28. The lateral portion 27 includes the lateral strap 17 and the lateral housing 15 and the medial portion 28 includes the medial strap 18 and the medial housing 14.

The strap assembly 12 includes at least two connectors 21, one connector 21 on each distal end 19 of the lateral strap 17 but the strap assembly 12 optionally may include more than two connectors 21 to allow the wheelchair maneuver assist device 10 to attach to a variety of handle grips 4 having various handle grip spans 7. In the preferred embodiment, the distal ends 19 of the lateral strap 17 contain a plurality of connectors 21, wherein the plurality of connectors 21 are a plurality of consecutively sewn together loops, or daisy chains, configured to enable the lateral strap 17 to span and connect between various pairs of handle grips 4 having handle grip spans 7 ranging from sixteen inches to thirty-four inches. In other embodiments, the lateral strap 17 is configured to span and connect between a pair of handle grips 4 having a handle grip span 7 less than sixteen inches, which is the case for some pediatric wheelchairs. In yet another embodiment, the lateral strap 17 is able to span and connect between a pair of handle grips 4 having a handle grip span more than thirty-four inches, which is the case for some geriatric wheelchairs. In the preferred embodiment, as shown in FIG. 2, each of the distal ends 19 of the lateral strap 17 contains five consecutive loops 21. In other embodiments (shown in FIG. 5) the distal ends 19 of the lateral strap 17 only contain a single loop 21. The connector 21, or loop, nearest the distal end 19 of the lateral strap 17 is configured to correspond with the connector 21, or loop, nearest the opposite distal end 19 to facilitate the connection of the lateral strap 17 between a pair of handle grips 4. The connector 21, or loop, nearest the distal end 20 of the lateral housing 13 is configured to correspond with the connector 21, or loop, nearest the opposite distal end 20 of the lateral housing 13 to facilitate the connection of the lateral strap 17 between a pair of handle grips 4. In other embodiments, the connector 21 may be located at each distal end 19 of the lateral strap 17 and include a single loop, handle grip clamps, hook and loop fasteners, button snaps, and so forth.

Figure 3A:
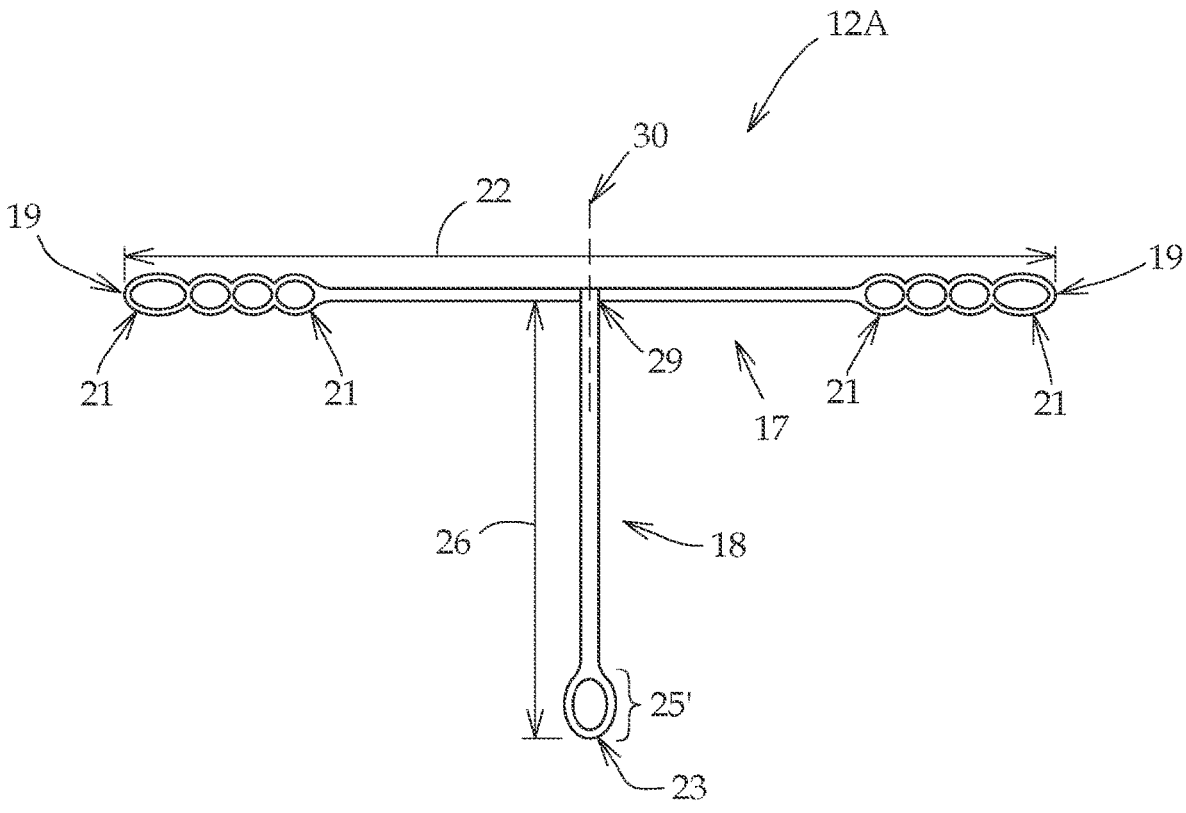
FIG. 3A pictures a top plan view of a strap assembly of the preferred embodiment of the wheelchair maneuver assist device of FIG. 1, wherein the lateral strap and medial strap are sewn together.

In the top plan view of FIG. 3A, an alternate embodiment of strap assembly 12 shows a proximal end 29 of the medial strap 18 connected to the lateral strap 17 to form T-shaped strap assembly 12A. In this embodiment, the lateral strap 17 has two distal ends 19 each including four connectors 21, depicted as four consecutive loops, and one medial strap 18 sewn to the lateral strap 17 near a midpoint 30 of the lateral strap 17. Further, the handle 25 is configured as a single loop handle 25' sewn at the distal end 23 of the medial strap 18. The lateral strap 17 may have any combination of loops 21 but includes at least one loop 21 at each distal end 19. Each distal end preferably contains an equal number of loops 21; however, the lateral strap 17 may include an unequal number of loops 21 at each distal end 19 without departing from the purpose and function of the connectors 21.

Figure 3B:
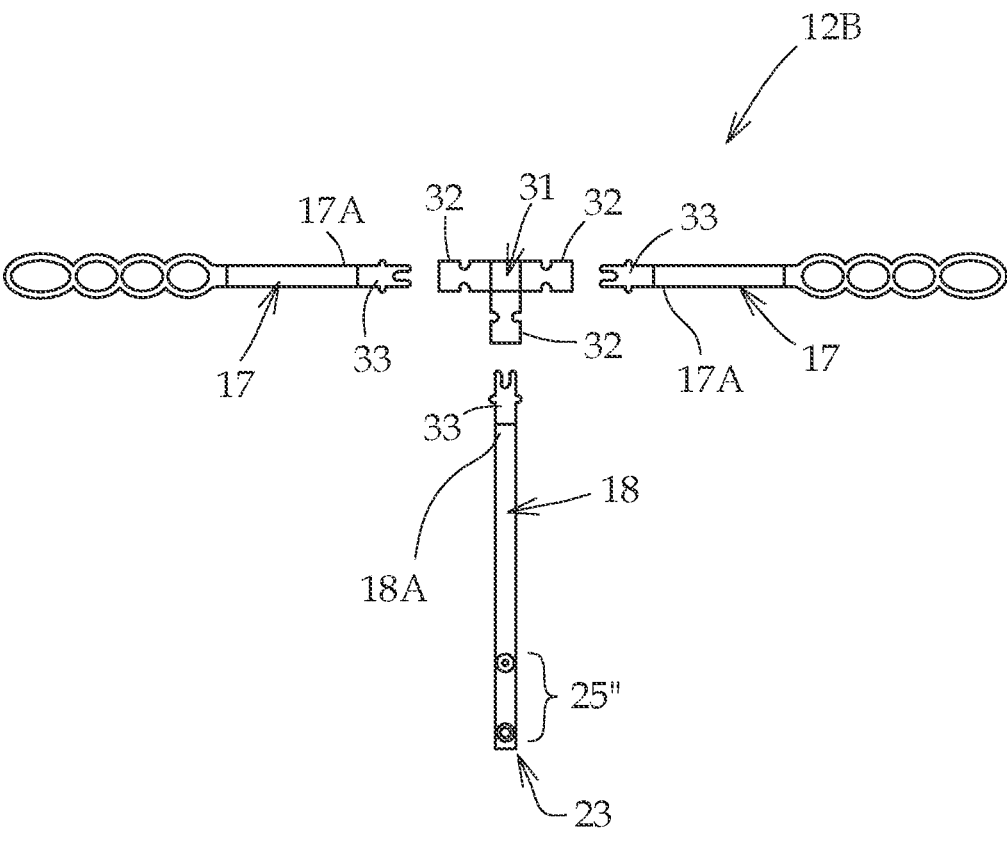
FIG. 3B pictures a top plan view of an alternative strap assembly, wherein a three-way, T-shaped strap connector having female buckles facilitates the connection between two lateral straps and one medial strap.

In FIG. 3B another embodiment is illustrated as strap assembly 12B which includes a three-way, T-shaped strap link 31 having three female buckles 32 wherein two lateral straps 17 and one medial strap 18, each having male buckles 33 located at proximal ends 17a, 18a respectively of straps 17, 18 are joined with the three-way, T-shaped strap link 31 to form the T-shaped strap assembly 12B. The three-way, T-shaped strap link 31 enables the caregiver 46 or patient 47 to repair or replace any strap 17, 18 without having to replace the entire wheelchair maneuver assist device 10, making it more affordable to repair and maintain. It shall be understood that the three-way, T-shaped strap link 31 may include three male buckles 33 and the two lateral straps 17 and one medial strap 18 would include female buckles 32. In this embodiment, the handle 25 is provided as a snap button handle 25" sewn into the distal end 23 of the medial strap 18 and as would be understood with conventional snap buttons, would be snapped together to form a loop at the end for grasping or could alternatively be snapped around the wrist of a user. Additional buttons may also be applied to the distal end 23 of the medial strap 18 to reinforce the support of the handle 25 when manipulated by the caregiver 46 and/or enable the caregiver to form a loop that conforms closely to the wrist of the caregiver.

Figure 3C:
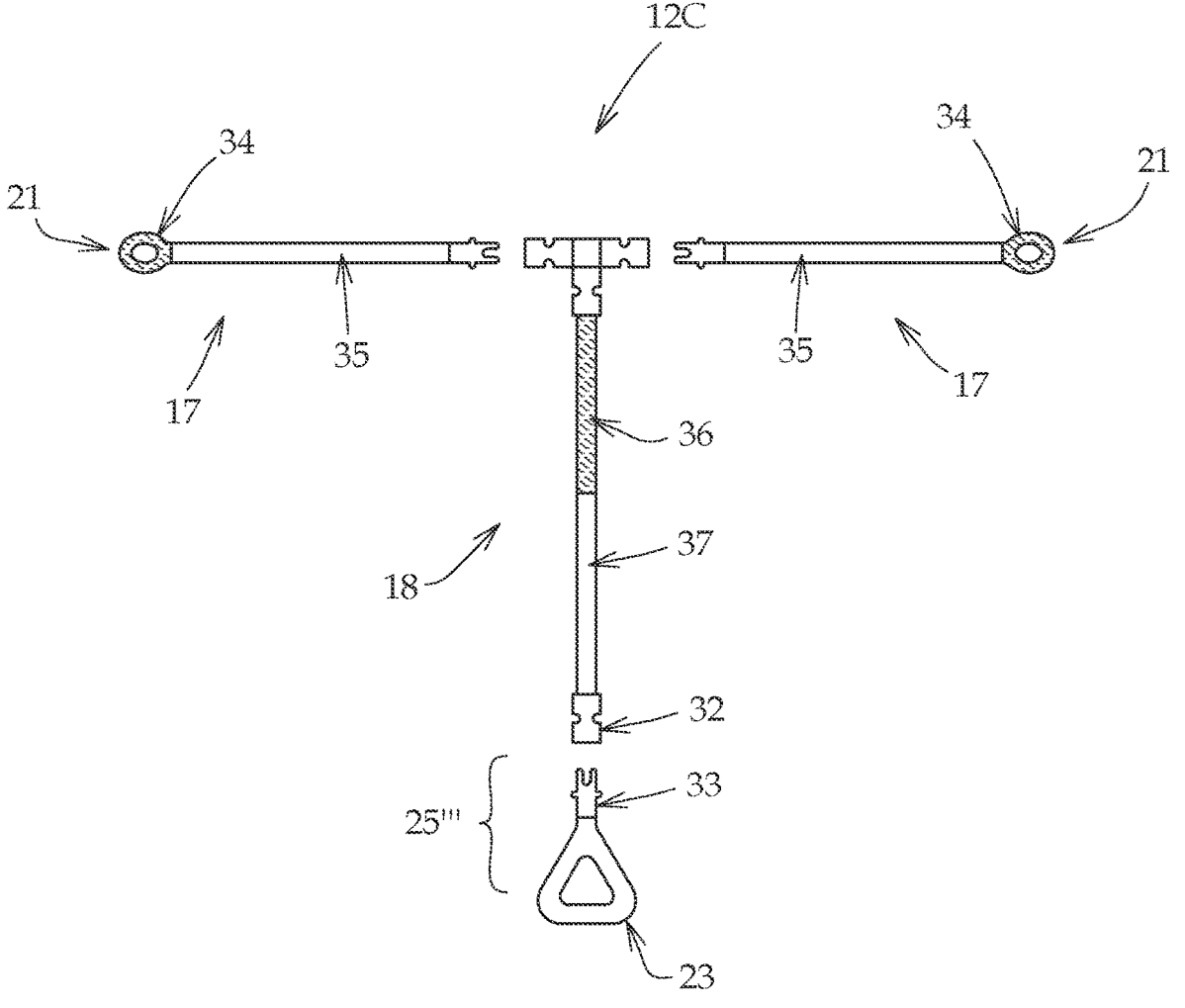
FIG. 3C pictures a top plan view of an alternative strap assembly of the embodiment in FIG. 3B, wherein the lateral strap includes an elastic lateral segment and a non-elastic lateral segment, and the medial strap includes an elastic medial segment and a non-elastic medial segment.

FIG. 3C depicts another alternate embodiment strap assembly 12C which may include an elastic lateral segment 34, non-elastic lateral segment 35, an elastic medial segment 36, and a non-elastic medial segment 37, to lengthen the lateral strap length 22 and medial strap length 26 respectively. The elastic segments are capable of easily stretching and returning to their original shape and size, while maintaining sufficient elasticity to enable the caregiver to pull the medial strap 18 or push the lateral portion 27 without causing any deformation of the strap assembly 12. Either one, both, or none of the elastic segments 34, 36 may be completely housed within the housing assembly 11 to further protect the elastic segments 34, 36 from wear and tear. The elastic medial segment 36 may be configured to stretch the medial strap 18 to an elongated state, thereby increasing the medial strap length 26 when the caregiver 46, or patient 47, pulls on the medial strap 18 to move the wheelchair 1 forward. When the medial strap 18 is no longer being pulled either by the caregiver 46 grasping the handle or by the patient 47 via attachment to a gait belt 48 posteriorly (not shown), the elastic medial segment 36 retracts and the medial strap 18 returns to the medial strap length 26. When the medial strap 18 is not being pulled, the medial strap length 26 does not exceed the handle grip height 8 to ensure that the medial strap 18 does not entangle with the wheelchair 1 and interfere with the normal movement of the wheelchair 1. The lateral strap 17 may include connectors 21 that are formed of an elastic material, thereby defining the elastic lateral segment 34, wherein the connectors 21 are a plurality of consecutively formed together elastic loops 21 configured to facilitate the connection of the lateral strap 17 between a pair of handle grips 4. In this embodiment, the handle 25 is shown as a rigid body handle 25''' shaped to be grasped by the caregiver 46 or patient 47. Although shown in a triangular configuration handle 25''' could be formed in a variety of shapes such as rectangular, circular, ovular or other wise to provide an easily graspable handle. During operation, the caregiver 46 may position their hand through the handle 25, or loop such that the handle 25, or loop is around their arm or wrist to allow the caregiver 46 to simultaneously provide hands on support to the patient 47 with both hands.

As illustrated in FIGS. 3A-C, the distal end 23 of the medial strap 18 includes a handle 25, whether it be handle 25', 25'', or 25'''. As would be understood, the handle 25 is preferably grasped by a single hand of the caregiver 46 (as shown in FIG. 5) while the opposite hand maintains proper contact and support with the patient 47; however, it should be noted that the handle 25 may also facilitate a connection between the medial strap 18 and the patient 47 such that the patient 47 may pull the wheelchair 1 forward without the assistance of the caregiver 46. The caregiver 46 may grasp the handle 25 with their hand, or in embodiments wherein the handle 25 is a loop, position their hand through the loop 25 such that the loop 25 is around their wrist and both hands are free to maintain proper and stable contact with the patient 47. When the handle 25 is connected with the gait belt 48, the connection is preferably easily removeable to allow the patient 47 to easily disconnect from medial strap 18. In yet another embodiment (not shown), the handle is a buckle component that is configured to join together with an opposing buckle either on the arm or wrist of the caregiver or on the gait belt 48 of the patient.

As pictured in the top plan views of FIGS. 2 and 4A-C, the housing assembly 11 may include various configurations, but ultimately includes the lateral housing 13 and the medial housing 14 coming together to form the T-shaped housing assembly 11. The housing assembly 11 is configured for the receipt of the strap assembly 12 to add some stability and partially protect the strap assembly 12 from wear and tear. As seen in FIG. 2, the lateral housing 13 defines a lateral housing length 15, the distance between the two distal ends 20 of the lateral housing 13, and the medial housing 14 defines a medial housing length 16, the distance between the proximal end 54 and distal end 24 of the medial housing 14.

FIG. 4A demonstrates alternate embodiment housing assembly 11A having lateral housing 13a and medial housing 14a. The proximal end 54a of medial housing 14a is configured to be insertable within a hole 38 defined near a midpoint 30 of lateral housing 13a. In this embodiment, lateral housing 13a is a hollow cylindrical pipe with a central hole on one side sized and shaped to receive and frictionally engage with medial housing 14a which is a second hollow cylindrical pipe.

FIG. 4B illustrates the preferred embodiment of housing assembly 11 also seen in FIG. 2 which includes a hollow, three-way, T-shaped housing link 39 having three openings 40, each opening 40 configured to receive a hollow cylindrical pipe to define the lateral housing 13 and medial housing 14. In the preferred embodiment, the lateral housing 13 includes two lateral hollow cylindrical pipes and the medial housing 14 includes one medial hollow cylindrical pipe.

The lateral housing 13 and medial housing 14 may be configured to enable lengthening and shortening of the lateral housing length 15 and medial housing length 16, respectively. As demonstrated in FIG. 4C, alternate embodiment housing assembly 11B depicts the lateral housing 13 and/or medial housing 14 having one or more inner housing pipes 41, 51 configured to telescopically slide within a slightly larger outer housing pipe 42, 52 (e.g., telescoping tubing) so that the one or more inner housing pipes 41, 51 can slide out of the slightly larger outer housing pipe 42, 52 to increase the lateral housing length 15 and medial housing length 16, respectively, based on a particular wheelchair handle grip span 7. The lateral housing length 15 is preferably 50%-90% the predetermined wheelchair handle grip span 7 but, in other embodiments, the lateral housing length 15 may span the entire handle grip span 7. As further shown in FIG. 4C, embodiments that include inner housing pipes 41, 51 and outer housing pipes 42, 52 may also include a locking mechanism 43, 53 for preventing sliding movement of the inner housing pipe 41, 51 and the slightly larger outer housing pipe 42, 52. In the preferred embodiment, the locking mechanism 43, 53 is a telescoping tube clamp configured to create a resistive clamping force on the inner housing pipe 41, 51 to restrict the sliding movement of the inner housing pipe 41, 51 and the slightly larger outer housing pipe 42, 52.

In some embodiments, the hollow, three-way, T-shaped housing link 39 may define the slightly larger outer housing pipe 42, 52, whereby the openings 40 defined in the hollow, three-way, T-shaped housing link 39 are slightly larger in diameter compared to the inner housing pipe 41, 51 diameter such that the inner housing pipe 41, 51 is capable of sliding in and out of the hollow, three way, T-shaped housing link 39. The inner housing pipe 41, 51 and outer housing pipes 42, 52 may be square pipes, cylindrical pipes, double concave pipes, bread pipes, single rib pipes, eccentric pipes, or any other pipe shape that forms a conduit capable of housing the strap assembly 12. The housing assembly 11 is made of a rigid material such as plastic, rubber, wood, metal, or any combination of these and similar materials. The housing assembly 11 may also be constructed of an antimicrobial or bacteria resistant material that is capable of protecting against the buildup of bacteria, mold, mildew, and other hazardous microbes.

As demonstrated in FIG. 5, once the wheelchair maneuver assist device 10 is connected between the pair of handle grips 4, the wheelchair maneuver assist device 10 may be configured to be positioned in an active state 44. During operation, the medial portion 28 (i.e., the medial strap 18 and the medial housing 14) is rotatably positioned over the seat 2 of the wheelchair 1 until the handle 25 (i.e., distal end 23 of the medial strap 18) is positioned near the front of the wheelchair 1, enabling a single caregiver 46 to pull the handle 25 with one hand and/or wrist so that the wheelchair 1 follows closely behind the patient 47 during mobility exercises in rehabilitation, home, or alternate settings. The caregiver 46 assisting the patient 47 may pull the handle 25 to propel the wheelchair 1 forward or turn the wheelchair 1 keeping the wheelchair 1 a safe distance behind the patient 47, while maintaining proper contact with the walking patient 47. The wheelchair 1 is a distance behind the patient 47 when the wheelchair 1 does not obstruct the mobility of the patient 47 or wheelchair 1 and when the patient 47 is able to safely descend into the seat 2 of the wheelchair 1. In an alternative method of operation (not shown), the handle 25, preferably a snap button configuration 25″, is connected directly to the patient 47, to a gait belt 48 for example, to enable a patient 47 to pull the wheelchair 1 without the need for a caregiver 46. During the active state 44, the medial strap 18 is pulled and the medial strap length 26 is increased or stretched without affecting the overall length or strength of the lateral strap 17.

As shown in FIG. 6, without removing the wheelchair maneuver assist device 10 from the wheelchair 1, the wheelchair maneuver assist device 10 may be reconfigured to be positioned in an inactive state 45 and is stowed away. When in inactive state 45, the medial portion 28 of the wheelchair maneuver assist device 10 is rotated around the lateral portion 27 until the medial portion 28 is positioned behind the backrest 3 such that the medial portion 28 dangles behind the seat 2 and backrest 3 of the wheelchair 1 so as to not obstruct the surface of the seat 2 or backrest 3 while the patient 47 is sitting down or interfere with the normal movement of the wheelchair 1 during daily wheelchair 1 mobility by patient 47. In embodiments having elastic medial segments 36, when positioned in the inactive state 45 (i.e., behind the backrest 3), the medial strap length 26 is not stretched, and the medial strap length 26 is less than the handle grip height 8 of the wheelchair 1 such that the medial strap 18 does not interfere with the movement of the wheelchair 1.

During either state (i.e., active 44 or inactive 45) the lateral housing 13 enables the caregiver 46 to easily push the wheelchair 1 with a single hand, if needed (not shown). Since the handle grips 4 of the wheelchair 1 are typically oriented parallel with one another and positioned near the outer edges of the wheelchair footprint, the caregiver 46 is often required to grasp both handles 4 to properly maneuver and control the motion of the wheelchair 1. Because of how handle grips 4 are typically oriented on the wheelchair 1, it can be very difficult to maneuver the wheelchair 1 with a single hand. In an effort to overcome this problem, the lateral housing 13 is configured (sized, shaped, otherwise capable of) to be pushed to thrust the wheelchair 1 forward. The lateral housing 13 is also configured to be pulled to reduce the acceleration of the wheelchair 1 when the wheelchair 1 is going down an incline, for example. Pushing the wheelchair 1 with the lateral housing 13, which is oriented perpendicular to the direction of motion, relieves strain on wrists and enables the caregiver 46 to push the wheelchair with a single hand, if needed, while still being able to properly maneuver and control the motion of the wheelchair 1. In embodiments wherein the lateral housing 13 includes at least one inner housing pipe 41 and an outer housing pipe 42 wherein the at least one inner housing pipe 41 is configured telescopically slidable within the outer housing pipe 42, the caregiver 46 or patient 47 may adjust the lateral housing length 15 to facilitate an alternative method of pushing the wheelchair 1.

The illustrations and examples provided herein are for explanatory purposes and are not intended to limit the scope of the appended claims. It will be apparent to those skilled in the art that various changes may be made without departing from the scope of the invention and the invention is not to be considered limited to what is shown and described in the specification and drawings.

The invention claimed is:

1. A wheelchair maneuver assist device (10) for assisting a caregiver (46) in maneuvering a wheelchair (1) behind a patient (47), the wheelchair maneuver assist device (10) comprising:
   a housing assembly (11) including a lateral housing (13) having two distal ends (20), and a medial housing (14) having a proximal end (54) configured to join the lateral housing (13) forming a T-shaped conduit;
   a strap assembly (12) including a lateral strap (17) having two distal ends (19) and a medial strap (18) having a proximal end (29) connected to the lateral strap (17) and a distal end (23) located opposite the proximal end (29);
   at least two connectors (21) located at the distal ends (19) of the lateral strap (17) and configured to facilitate the connection of the lateral strap (17) between a pair of handle grips (4) of the wheelchair (1); and
   a handle (25) located at the distal end (23) of the medial strap (18) to facilitate the grasping and pulling of the medial strap (18),
   wherein the lateral strap (17) includes an elastic lateral segment (34) and a non-elastic lateral segment (35), and wherein the distance between the distal ends (19 of the lateral strap (17) when the elastic lateral segment (34) is not stretched defines a lateral strap length (22).

2. The wheelchair maneuver assist device (10) of claim 1, wherein the housing assembly (11) includes a hollow three-way, T-shaped, housing link (39) configured to receive two lateral housings (13) in series, defined by two lateral cylindrical pipes, and one medial housing (14) defined by one medial cylindrical pipe to form the T-shaped conduit configured to receive the strap assembly (12).

3. The wheelchair maneuver assist device (10) of claim 1, wherein the lateral housing (13) includes at least one inner housing pipe (41), at least one outer housing pipe (42), and a locking mechanism (43), wherein the at least one inner housing pipe (41) is configured to telescopically slide within the at least one outer housing pipe (42), and wherein the locking mechanism (43) is configured to create a resistive clamping force on the at least one inner housing pipe (41) to restrict the sliding movement of the at least one inner housing pipe (41) and the at least one outer housing pipe (42).

4. The wheelchair maneuver assist device (10) of claim 1, wherein the medial housing (14) includes at least one inner housing pipe (51), at least one outer housing pipe (52), and a locking mechanism (53), wherein the at least one inner housing pipe (51) is configured to telescopically slide within the at least one outer housing pipe (52), and wherein the locking mechanism (53) is configured to create a resistive clamping force on the at least one inner housing pipe (51) to restrict the sliding movement of the at least one inner housing pipe (51) and the at least one outer housing pipe (52).

5. The wheelchair maneuver assist device (10) of claim 1, wherein the lateral strap length (22) is twelve inches, and the lateral strap length (22) can be lengthened up to thirty-four inches when the elastic lateral segment (34) is fully stretched.

6. The wheelchair maneuver assist device (10) of claim 1, wherein the medial strap (18) includes an elastic medial segment (36), and wherein the distance between the proximal end (29) and distal end (23) of the medial strap (18) when the elastic medial segment (36) is not stretched defines a medial strap length (26).

7. The wheelchair maneuver assist device (10) of claim 6, wherein the medial strap length (26) is twelve inches, and the medial strap length (26) can be lengthened to forty inches when the elastic medial segment (36) is fully stretched.

8. The wheelchair maneuver assist device (10) of claim 1, wherein the housing assembly (11) is formed from an antimicrobial material.

9. The wheelchair maneuver assist device (10) of claim 1, wherein the at least two connectors (21) located at the distal ends (19) of the lateral strap (17) is a sewn loop.

10. The wheelchair maneuver assist device (10) of claim 1, wherein the at least two connectors (21) located at the distal ends (19) of the lateral strap (17) is a plurality of consecutively sewn together loops.

11. The wheelchair maneuver assist device (10) of claim 1, wherein the handle (25) located at the distal end (23) of the medial strap (18) is a sewn loop.

12. The wheelchair maneuver assist device (10) of claim 1, wherein the handle (25) located at the distal end (23) of the medial strap (18) is a button and snap configuration sewn into the distal end (23) of the medial strap (18).

13. A wheelchair maneuver assist device (10) for assisting a caregiver (46) maneuvering a wheelchair (1) behind a patient (47), the wheelchair maneuver assist device (10) comprising:

a strap assembly (12) including a lateral strap (17) defining a lateral strap length (22) and a medial strap (18) defining a medial strap length (26), the lateral strap (17) and medial strap (18) are connected together to form a T-shaped strap assembly (12);

a housing assembly (11) including a hollow, three-way, T-shaped, housing link (39) configured to receive two lateral housing pipes (13) in series, together defining a lateral housing length (15), and one medial housing pipe (14) defining a medial housing length (16) to form a T-shaped housing assembly (11) configured to receive the T-shaped strap assembly (12) to partially protect the strap assembly (12) from wear and tear, wherein either the lateral strap (17) includes an elastic lateral segment (34), and the medial strap (18) includes an elastic medial segment (36), or the lateral strap (17) includes the elastic medial segment (36) and the medial strap (18) includes the elastic lateral segment (34);

wherein the lateral strap length (22) is longer than the lateral housing length (13), and wherein the medial strap length (26) is longer than the medial housing length (16).

14. The wheelchair maneuver assist device (10) of claim 13, wherein the lateral housing (13) includes at least one inner housing pipe (41), at least one outer housing pipe (42), and a locking mechanism (43), wherein the at least one inner housing pipe (41) is configured to telescopically slide within the at least one outer housing pipe (42), and wherein the locking mechanism (43) is configured to create a resistive clamping force on the at least one inner housing pipe (41) to restrict the sliding movement of the at least one inner housing pipe (41) and the at least one outer housing pipe (42).

15. The wheelchair maneuver assist device (10) of claim 13, wherein the medial housing (14) includes at least one inner housing pipe (51), at least one outer housing pipe (52), and a locking mechanism (53), wherein the at least one inner housing pipe (51) is configured to telescopically slide within the at least one outer housing pipe (52), and wherein the locking mechanism (53) is configured to create a resistive clamping force on the at least one inner housing pipe (51) to restrict the sliding movement of the at least one inner housing pipe (51) and the at least one outer housing pipe (52).

16. The wheelchair maneuver assist device (10) of claim 13, further comprising a handle (25) located at a distal end (23) of the medial strap (18), wherein the handle (25) is a sewn loop.

17. The wheelchair maneuver assist device (10) of claim 13, wherein the housing assembly (11) is formed from an antimicrobial material.

18. The wheelchair maneuver assist device (10) of claim 13, further comprising a handle (25) located at a distal end (23) of the medial strap (18), wherein the handle (25) is a button and snap configuration sewn into the distal end (23) of the medial strap (18).

19. The wheelchair maneuver assist device (10) of claim 13 further including at least two connectors (21) located at distal ends (19) of the lateral strap (17) and configured to facilitate the connection of the lateral strap (17) between a pair of handle grips (4) of the wheelchair (1).

\* \* \* \* \*